United States Patent
Ahn et al.

(10) Patent No.: US 11,389,092 B2
(45) Date of Patent: Jul. 19, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: Sung Mo Ahn, Yongin-si (KR); Hyeong Seok Jang, Seoul (KR); Sang Kyu Kim, Yongin-si (KR); Jin Young Park, Hwaseong-si (KR); Jun Ho Lee, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 211 days.

(21) Appl. No.: 16/816,415

(22) Filed: Mar. 12, 2020

(65) Prior Publication Data

US 2021/0052200 A1 Feb. 25, 2021

(30) Foreign Application Priority Data

Aug. 20, 2019 (KR) .......................... 10-2019-0101666

(51) Int. Cl.
*A61B 5/1455* (2006.01)
*A61B 5/00* (2006.01)
*A61B 5/145* (2006.01)

(52) U.S. Cl.
CPC .......... *A61B 5/1455* (2013.01); *A61B 5/0075* (2013.01); *A61B 5/14532* (2013.01); *A61B 5/6824* (2013.01); *A61B 5/74* (2013.01); *A61B 2562/02* (2013.01)

(58) Field of Classification Search
CPC . A61B 5/1455; A61B 5/14532; A61B 5/6824; A61B 5/74; A61B 5/0075; A61B 2562/02
See application file for complete search history.

(56) References Cited

U.S. PATENT DOCUMENTS

| 6,167,290 | A | 12/2000 | Yang et al. |
| 6,205,354 | B1 | 3/2001 | Gellermann et al. |
| 6,223,063 | B1 * | 4/2001 | Chaiken ............ A61B 5/14532 600/310 |
| 6,341,257 | B1 | 1/2002 | Haaland |
| 6,711,503 | B2 | 3/2004 | Haaland |

(Continued)

FOREIGN PATENT DOCUMENTS

| CA | 2 363 417 A1 | 9/2000 |
| ER | 3 127 480 A1 | 2/2017 |

(Continued)

OTHER PUBLICATIONS

Derek Jones, "The Blood Volume Pulse—Biofeedback Basics", (Fixxl Ltd) May 10, 2018, pp. 1-4, 4 pages total.

(Continued)

*Primary Examiner* — Eric F Winakur
(74) *Attorney, Agent, or Firm* — Sughrue Mion, PLLC

(57) ABSTRACT

An apparatus for estimating bio-information according to an embodiment of the present disclosure includes a processor configured to obtain spectra from an object, obtain a component produced based on a change in pressure applied to the object, correct the spectra based on the obtained component produced based on the change in pressure, and estimate bio-information of the object based on the corrected spectra.

25 Claims, 14 Drawing Sheets

(56) References Cited

U.S. PATENT DOCUMENTS

| | | | |
|---|---|---|---|
| 2004/0068163 | A1 | 4/2004 | Ruchti et al. |
| 2011/0028808 | A1 | 2/2011 | Kuratsune et al. |
| 2011/0184683 | A1* | 7/2011 | Soller ............... G01N 21/3577 702/85 |
| 2012/0316848 | A1 | 12/2012 | Noh et al. |
| 2012/0330164 | A1 | 12/2012 | Ermakov et al. |
| 2014/0372081 | A1 | 12/2014 | Izzetoglu et al. |
| 2016/0089088 | A1 | 3/2016 | Kim et al. |
| 2017/0143210 | A1 | 5/2017 | Ikebe |
| 2018/0146899 | A1 | 5/2018 | Lee et al. |
| 2018/0202938 | A1 | 7/2018 | Cardoso-Menezes et al. |
| 2018/0242901 | A1 | 8/2018 | Barnes et al. |
| 2019/0150746 | A1 | 5/2019 | Kim |

FOREIGN PATENT DOCUMENTS

| | | |
|---|---|---|
| JP | 2005-233681 A | 9/2005 |
| JP | 2010-264276 A | 11/2010 |
| JP | 5047962 B2 | 10/2012 |
| KR | 10-0694598 B1 | 3/2007 |
| KR | 10-2012-0137828 A | 12/2012 |
| WO | 2012/135413 A1 | 10/2012 |
| WO | 2019/049117 A1 | 3/2019 |

OTHER PUBLICATIONS

Jian Shao et al., "Pulse Oximeter Based Heart Beats Rate Monitor", EE6350 VLSI Design Lab, Electrical Engineering, 2014, 3 pages total.

Alexey Popov et al., "Influence of probe pressure on diffuse reflectance spectra of human skin measured in vivo", Journal Of Biomedical Optics, vol. 22, No. 11, DOI: 10.1117/1.JB0.22.11.110504, ISSN: 1083-3668, Nov. 20, 2017, pp. 1-4, 4 pages total, XP055734396.

Spigulis et al., "Contact probe pressure effects in skin multi-spectral photoplethysmography", Proceedings of SPIE—The International Society for Optical Engineering, DOI: 10.1117/12.727985, ISSN: 0277-786X, Jun. 2007, 9 pages total, XP055734469.

Tianming Zhao et al., "PPG-based Finger-level Gesture Recognition Leveraging Wearables", IEEE INFOCOM 2018, IEEE Conference On Computer Communications, Apr. 2018, DOI: 10.1109/INFOCOM.2018.8486006, ISBN: 978-1-5386-4128-6, pp. 1457-1465, 9 pages total, XP055734330.

K. Gerrit Held et al., "Multiple irradiation sensing of the optical effective attenuation coefficient for spectral correction in handheld OA imaging", Photoacoustics, vol. 4, No. 2, Jun. 4, 2016, DOI: 10.1016/j.pacs.2016.05.004, ISSN: 2213-5979, pp. 70-80, 11 pages total, XP055734446.

Communication dated Oct. 8, 2020 issued by the European Intellectual Property Office in counterpart European Application No. 20174103.0.

* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2019-0101666, filed on Aug. 20, 2019, in the Korean Intellectual Property Office, the disclosure of which is incorporated by reference herein in its entirety.

BACKGROUND

1. Field

The following description relates generally to an apparatus and method for estimating bio-information, and more particularly to technology for correcting a component, produced due to a change in pressure applied by an object to a spectrometric sensor, in a spectrum obtained from the object.

2. Description of Related Art

Recently, research has been conducted on methods for non-invasively measuring bio-information, such as blood glucose, by using Raman spectroscopy or near-infrared spectroscopy. Bio-information measuring devices using spectroscopic techniques generally include a light source for emitting light toward an object, and a detector for detecting an optical signal reflected by the object. The bio-information measuring devices reconstruct spectra by using the optical signal detected by the detector, and measure biological components in the body, such as carotenoid, blood glucose, calories, and the like, by analyzing the reconstructed spectra. Light absorption by hemoglobin in the blood affects the entire skin spectrum. Accordingly, in order to minimize the absorption of light by hemoglobin in the blood, certain optical sensors apply pressure greater than or equal to a predetermined value to the skin when measuring an optical spectrum skin. These sensors may include a pressure sensor, a force sensor, and the like, to improve accuracy. However, the sensors might not be capable of being manufactured in a compact size. Additionally, the usage of such sensors might increase the measurement time.

SUMMARY

According to an aspect of the disclosure, an apparatus for estimating bio-information includes a processor configured to obtain spectra from an object, obtain a component produced based on a change in pressure applied to the object, correct the spectra based on the obtained component produced based on the change in pressure, and estimate bio-information of the object based on the corrected spectra.

The processor may perform principal component analysis (PCA) on the obtained spectra, and the processor may obtain the component, produced based on the change in pressure, based on a result of performing the PCA.

The processor may obtain the component, produced based on the change in pressure, based on a shape of components which are analyzed by using the PCA.

The processor may obtain a component, having a shape similar to a hemoglobin absorption peak among the components analyzed by using the PCA, as the component produced based on the change in pressure.

The processor may obtain a component, having a spectrum shape similar to that of a component defined in a component database among the components analyzed by the PCA, as the component produced based on the change in pressure.

The processor may obtain a component, produced based on another change in pressure applied by the object to a spectrometric sensor, from a component database.

The processor may collect spectra, obtained from a plurality of subjects, as training data, perform principal component analysis (PCA) on the collected training data, and store a spectrum shape of principal components and principal component scores in the component database based on performing the PCA.

The processor may perform the PCA on the obtained spectra from the object, and update the component database by using the components analyzed by using the PCA.

The processor may determine whether to update the component database based on at least one of a PCA result of the spectra obtained from the object, a generation date and an update date of the component database, and a collection environment of the training data.

The apparatus may include a communication interface which, in response to determining to update the component database, receives a component database from an external device.

The processor may correct a spectrum change caused by the change in pressure by removing the component, produced based on the change in pressure, from the obtained spectra.

The processor may remove the obtained component from the obtained spectra by using a least square method.

The processor may obtain the component, produced based on the change in pressure, based on spectra obtained during an initial pressure phase of an entire time period in which the spectra are obtained.

The processor may obtain a noise-related component of the obtained spectra, and correct the obtained spectra based on the component produced based on the change in pressure and the noise-related component.

Based on a correlation between principal component scores of principal components, which are analyzed by performing principal component analysis on at least one spectrum of the obtained spectra, and an estimated bio-information value which is estimated based on the at least one spectrum of the spectra, the processor may obtain at least one of the component produced based on the change in pressure and the noise-related component.

The bio-information of the object may include at least one of blood glucose, triglyceride, cholesterol, calories, protein, carotenoid, lactate, and uric acid.

A method of estimating bio-information of an object includes obtaining spectra from an object, obtaining a component produced based on a change in pressure applied to the object, correcting the spectra based on the obtained component produced based on the change in pressure, and estimating the bio-information the object based on the corrected spectra.

The method may include performing principal component analysis (PCA) on the obtained spectra, and obtaining the component, produced based on the change in pressure, based on a result of the PCA.

The obtaining of the component produced based on the change in pressure may include obtaining the component, produced based on the change in pressure, based on a shape of components which are analyzed by using the PCA.

The obtaining of the component produced due to the change in pressure may include obtaining a component, having a shape similar to a hemoglobin absorption peak among the components analyzed by using the PCA, as the component produced based on the change in pressure.

The obtaining of the component produced based on the change in pressure may include obtaining a component, having a spectrum shape similar to that of a component defined in a component database among the components analyzed by the PCA, as the component produced based on the change in pressure.

The obtaining of the component produced based on the change in pressure may include obtaining a component, produced based on a change in pressure applied by the object to a spectrometric sensor, from the component database.

The correcting of the spectra may include correcting a spectrum change caused by the change in pressure by removing the component, produced based on the change in pressure, from the obtained spectra.

The obtaining of the component produced based on the change in pressure may include obtaining the component, produced based on the change in pressure, based on spectra obtained during an initial pressure phase of an entire time period in which the spectra are obtained.

The method may include obtaining a noise-related component of the obtained spectra, and the correcting of the spectra may include correcting the obtained spectra based on the component produced based on the change in pressure and the noise-related component.

The obtaining of the noise-related component may include obtaining the noise-related component based on a correlation between principal component scores of principal components, which are analyzed by performing principal component analysis on at least one spectrum of the obtained spectra, and an estimated bio-information value which is estimated based on the at least one spectrum of the spectra.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings and the detailed description, unless otherwise described, the same drawing reference numerals may refer to the same elements, features, and structures. The relative size and depiction of these elements may be exaggerated for clarity, illustration, and convenience.

DETAILED DESCRIPTION

Figure 1:
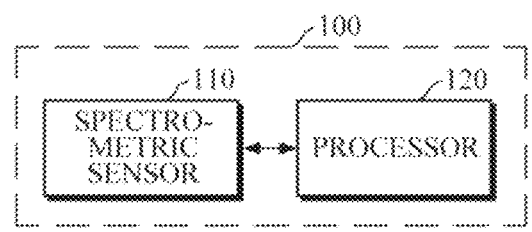
FIG. 1 is a block diagram illustrating an apparatus for estimating bio-information according to an embodiment.

Details of other embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals may refer to the same elements, features, and structures.

It will be understood that, although the terms "first," "second," etc. may be used herein to describe various elements, these elements should not be limited by these terms. These terms may be used to distinguish one element from another. Any references to the singular form of a term may include the plural form of the term unless expressly stated otherwise. In addition, unless explicitly described to the contrary, an expression such as "comprising" or "including" may imply the inclusion of the stated elements but not the exclusion of any other elements. Also, the terms such as "part," "module," etc., may refer to a unit that performs at least one function or operation and that may be embodied as hardware, software, or a combination thereof.

Hereinafter, embodiments of an apparatus and method for estimating bio-information will be described in detail with reference to the accompanying drawings.

FIG. 1 is a block diagram illustrating an apparatus for estimating bio-information according to an embodiment of the present disclosure.

Referring to FIG. 1, the apparatus 100 for estimating bio-information includes a spectrometric sensor 110 and a processor 120.

The spectrometric sensor 110 may continuously obtain spectrum data from an object for a predetermined period of time. In this case, the object may be, for example, skin tissue of the human body, such as the wrist, fingers, and the like, at which veins or capillaries are located, or may be an area on the wrist which is adjacent to the radial artery. However, the object is not limited thereto. The spectrometric sensor 110 may measure a spectrum by using Diffuse reflectance spectroscopy, Absorption spectroscopy, Raman spectroscopy, Near Infrared spectroscopy, or Mid Infrared spectroscopy.

The spectrometric sensor 110 may include one or more light sources configured to emit light toward the object, and one or more detectors configured to detect light scattered by or reflected from the object. The light source may include a light emitting diode (LED), a laser diode, a phosphor, and the like. The plurality of light sources may emit light of different wavelengths. In this case, a color filter for transmitting or blocking light in a specific wavelength region may be disposed at the top of at least one of the light sources.

The detector may include one pixel or an array of two or more pixels, each of which may include a photo diode or a photo transistor. Based on detecting light, the detector may convert the detected light signal into an electric signal. A collimator, such as a microlens, and the like, which improves light collection efficiency, may be disposed at the top of each pixel.

Based on receiving a request for measuring a spectrum, the processor 120 may control the spectrometric sensor 110. Based on the request for measuring a spectrum, the processor 120 may output information that guides a user to touch the spectrometric sensor 110 with an object, and to change pressure applied to the spectrometric sensor 110 for a predetermined period of time.

Based on the user touching the spectrometric sensor 110 with the object and changes contact pressure for a predetermined period of time, the spectrometric sensor 110 may emit light toward the object for a predetermined period of time, and may detect light reflected by the object.

Based on receiving spectrum data from the spectrometric sensor 110, the processor 120 may recover a spectrum based on the received spectrum data.

Figure 2:
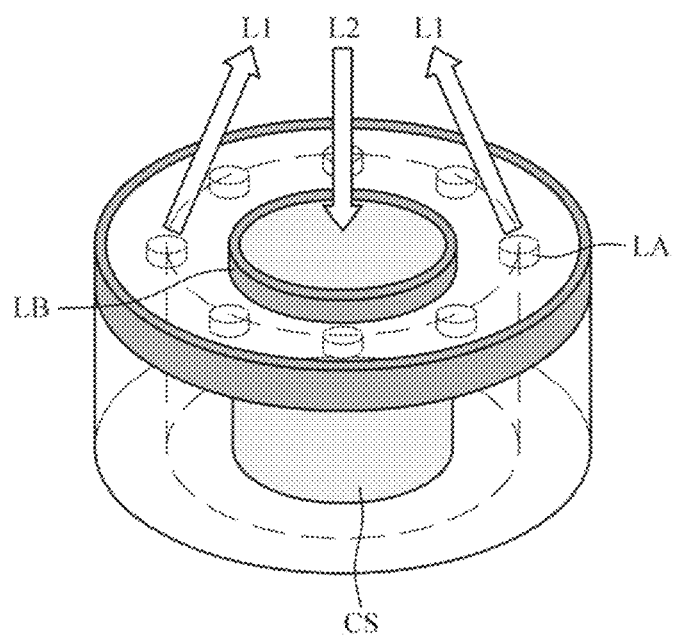
FIG. 2 is a diagram schematically illustrating an example of a structure of a spectrometric sensor according to an embodiment.

FIG. 2 is a diagram schematically illustrating an example of a structure of a spectrometric sensor 110. The structure of the spectrometric sensor 110 illustrated in FIG. 2 is merely an example, such that the spectrometric sensor 110 is not limited thereto and may have various other structures.

Referring to FIG. 2, the spectrometric sensor 110 according to an embodiment includes an LED array LA having n number of LED light sources arranged on a circular frame. Here, a shape of the frame is not limited to a circular shape, but may be modified depending on the shape of the apparatus 100 for estimating bio-information.

Each LED light source may have at least some peak wavelengths in different wavelength bands. For example, each LED light source may simultaneously or sequentially emit light toward the object OBJ. The peak wavelength of each LED light source may be preset, and may be set based on a spectrum measurement portion, a target component to be analyzed, and the like. After light is emitted by each of the LED light sources toward the object, the emitted light is absorbed into, or reflected or scattered from, the object depending on tissue properties of the object. In this case, photoreaction properties of the object may vary depending on the types of the object and the wavelengths of light, and the degree of absorption, reflection, transmission, or scattering of light by the object may vary depending on the photoreaction properties of the object. Further, the spectrometric sensor 110 may include a detector CS which is disposed at the center of the circular frame, and detects scattered or reflected light L2 when light L1 is emitted by the LED light source LA toward the object and is scattered or reflected from the object. For example, the detector CS may be a sensor based on a complementary metal-oxide-semiconductor (CMOS) Image Sensor (CIS), and a spectroscopic filter for detecting light of various wavelengths may be disposed on the CIS, but the detector CS is not limited thereto.

In addition, the spectrometric sensor 110 may include a light blocking part (LB) which prevents light, emitted by the LED light source LA, from being emitted directly toward the detector CS without first being emitted toward the object, and which directs light scattered by or reflected from the object toward the detector CS.

Based on obtaining a spectrum from the spectrometric sensor 110, the processor 120 may process the spectrum to analyze bio-information, such as a body surface component or an in vivo component, from the object, and may estimate bio-information by using the processed spectrum. In this case, the bio-information may include, for example, blood glucose, calories, alcohol, triglyceride, protein, cholesterol, uric acid, carotenoid, and the like, but is not limited thereto.

When light is emitted by the light source of the spectrometric sensor 110 toward the object and is absorbed into or scattered by or reflected from body tissue, light absorption by hemoglobin in the blood significantly affects the entire skin spectrum. Generally, when a spectrum is measured from an object, pressure greater than or equal to a predetermined value may be applied to the object to minimize absorption of light by hemoglobin in the blood. However, a spectrum may be changed when pressure is applied to the object, and the spectrum is changed dynamically according to the intensity of pressure applied to the object, a period of time of applying pressure, and the like.

In a spectrum which is obtained continuously by the spectrometric sensor 110 during a predetermined period of time (hereinafter referred to as a "first spectrum"), the processor 120 may correct a spectrum change caused by a change in pressure applied to the object when the object presses the spectrometric sensor 110.

For example, the processor 120 may extract a component produced due to a pressure change of the object (hereinafter referred to as a "pressure component") from the first spectrum, and may correct the first spectrum based on the extracted pressure component. For example, the processor 120 may extract the pressure component from the entire first spectrum or a part of the first spectrum (hereinafter referred to as a "second spectrum") by using principal component analysis. In this case, the second spectrum may be a spectrum obtained in an initial pressure phase when pressure starts to be applied after the object comes into contact with the spectrometric sensor 110. The initial pressure phase may be predetermined, and may be adjusted properly by considering a spectrum processing speed and/or a bio-information estimation speed.

Further, based on extracting the pressure component, the processor 120 may remove the pressure component from the entire first spectrum or from a spectrum obtained after the initial pressure phase, and thus may obtain a spectrum which is less affected by the pressure change of the object.

Figure 3A:
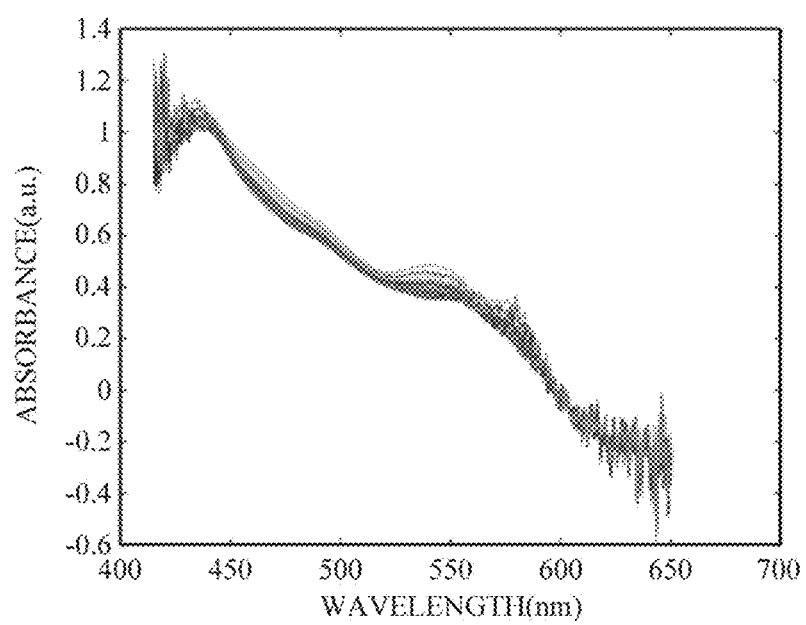
FIGS. 3A to 3C are diagrams explaining an example of correcting a spectrum by using principal component analysis according to an embodiment.
Figure 3B:
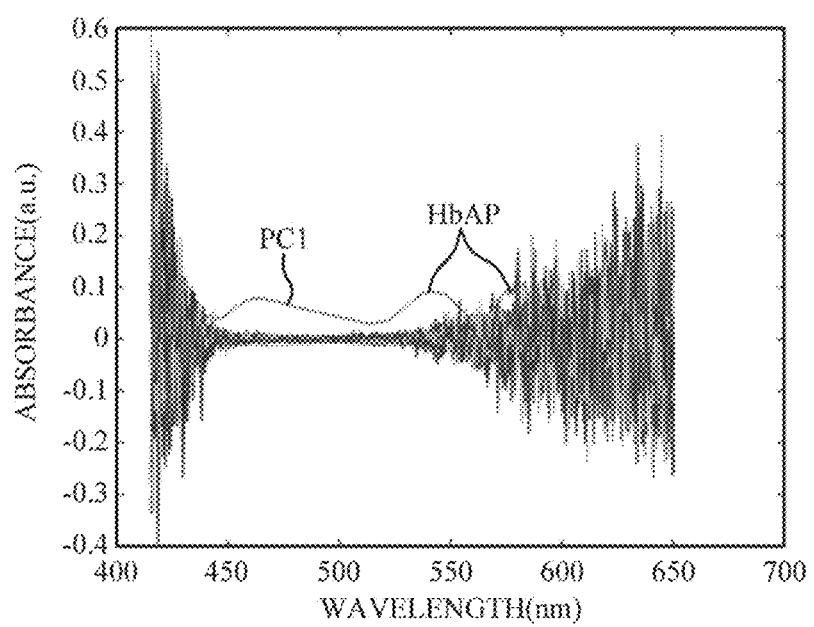
Figure 3C:
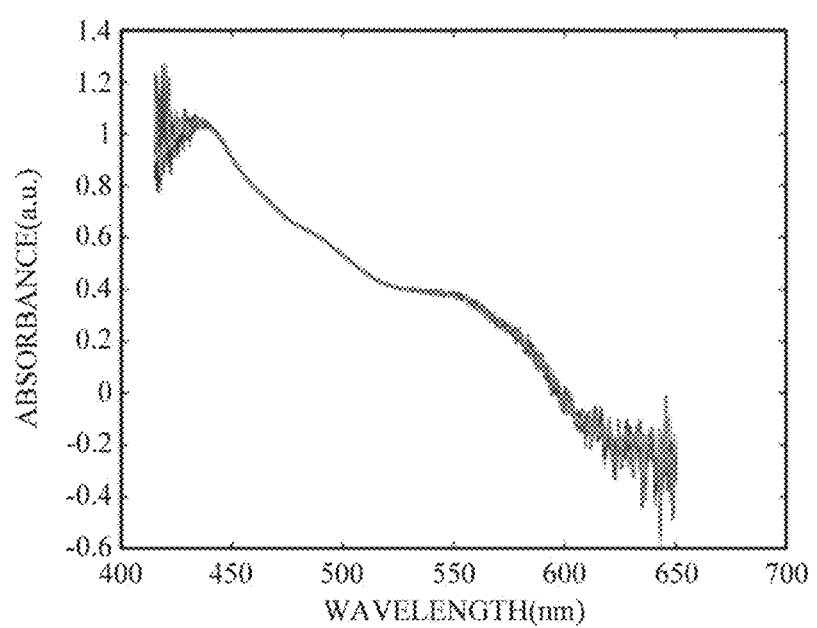

FIGS. 3A to 3C are diagrams explaining an example of correcting a spectrum by using principal component analysis.

FIG. 3A is a diagram illustrating a first spectrum obtained by the spectrometric sensor 110 for a predetermined period of time, and FIG. 3B is a diagram illustrating a result of principal component analysis of a second spectrum obtained in an initial pressure phase. As illustrated in FIGS. 3A and 3B, the processor 120 may extract a pressure component PC1 produced due to a pressure change of the object from the result of principal component analysis. The processor 120 may extract the pressure component PC1 based on a spectrum shape of principal components. By comparing the spectrum shape of the principal components, which are analyzed by using principal component analysis, with a hemoglobin absorption peak HbAP, the processor 120 may extract a principal component, having a shape similar to the hemoglobin absorption peak, as the pressure component PC1 of the object. In this case, pre-set information may be used as the hemoglobin absorption peak HbAP.

FIG. 3C is a diagram illustrating a spectrum after correction. Based on extracting the pressure component by using principal component analysis, the processor 120 may remove the pressure component PC1 from the first spectrum by using, for example, a least square method, and the like. Referring to FIGS. 3B and 3C, it can be seen that a predetermined wavelength range in the first spectrum (a range of about 430 nm to 570 nm), i.e., a wavelength range which is affected by the pressure change of the object, is corrected by principal component analysis.

Further, the processor 120 may remove noise, which causes a spectrum change other than the spectrum change caused by the pressure change, from the first spectrum. For example, noise may include various factors, such as temperature, humidity, motion noise, detector noise, light source noise, and the like, which affect spectrum accuracy, but is not limited thereto.

For example, the processor 120 may extract a noise component based on a correlation between principal component scores of principal components, which are analyzed by using principal component analysis, and estimated bio-information values which are estimated based on a spectrum before correction. In this case, the correlation may include at least one of Euclidean distance, Pearson correlation coefficient, Spearman correlation coefficient, and Cosine similarity, but is not limited thereto.

Figure 4A:
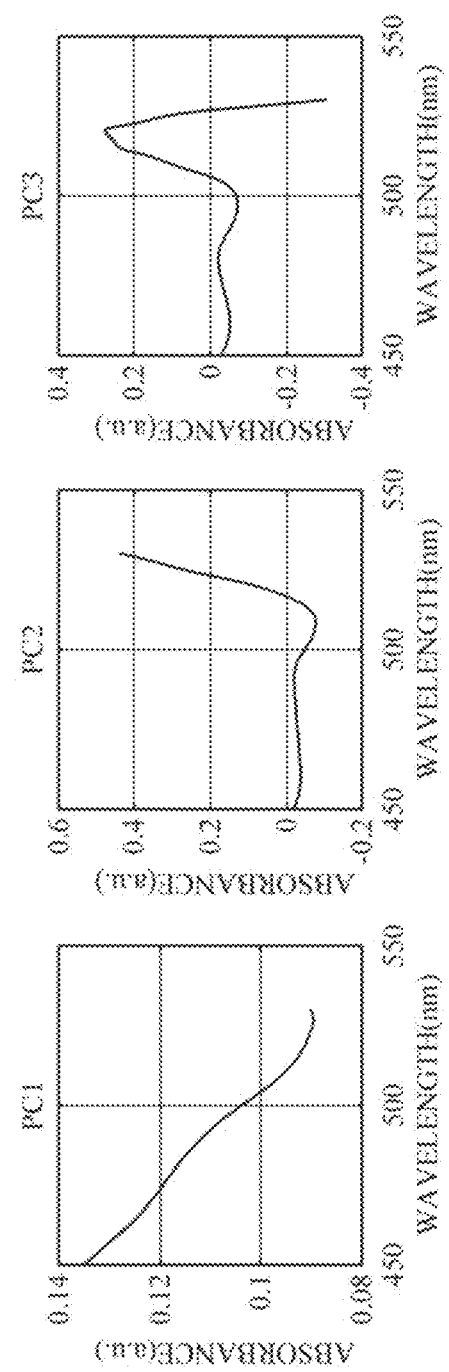
FIG. 4A to 4D are diagrams explaining another example of correcting a spectrum by using principal component analysis according to an embodiment.
Figure 4B:
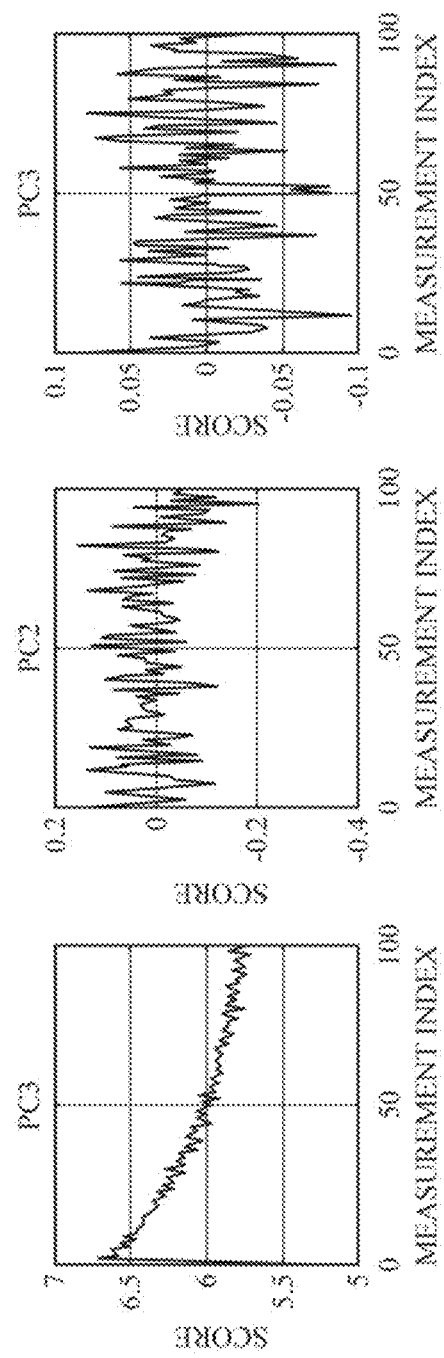
Figure 4C:
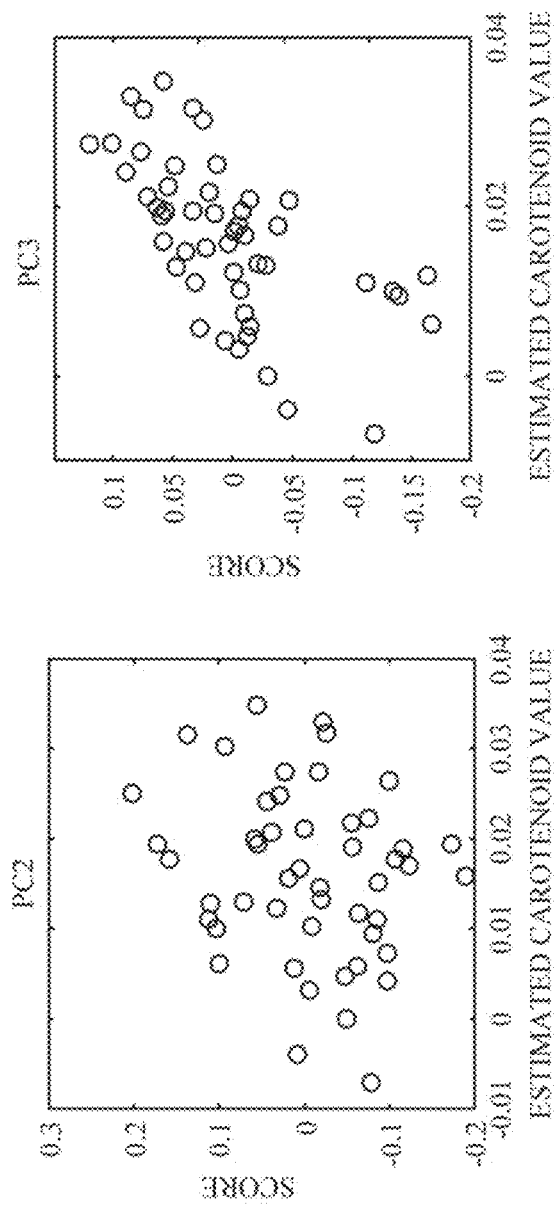

FIG. 4A to 4C are diagrams explaining another example of correcting a spectrum by using principal component analysis.

FIG. 4A is a diagram illustrating characteristics of three principal components PC1, PC2, and PC3 for each wavelength, which are obtained by principal component analysis of 100 second spectra obtained in an initial pressure phase. Here, it is assumed that the first component PC1 is a pressure component. FIG. 4B illustrates principal component scores of the principal components PC1, PC2, and PC3 which are extracted from each of the 100 second spectra of FIG. 4A. Here, the X axis represents the number of times the principal components are analyzed, which indicates, for example, the principal components are analyzed 100 times by using each of the 100 spectra; and the Y axis represents the principal component scores of each of the analyzed principal components.

As described above, the processor 120 may analyze the principal components by using each of the 100 second spectra in the initial pressure phase, and may estimate carotenoid. Particularly, various noise, such as contact failure and the like, may be present in the initial pressure phase, such that accuracy of the second spectra may be reduced. If carotenoid is estimated by using each second spectrum including the noise component, the estimated values do not fall within a predetermined range and may fluctuate significantly. Accordingly, in the case where there is a high correlation between a fluctuation shape of the estimated carotenoid values and the principal component scores, the processor 120 may determine the principal component to be a factor that causes fluctuation in the estimated carotenoid values.

Figure 4D:
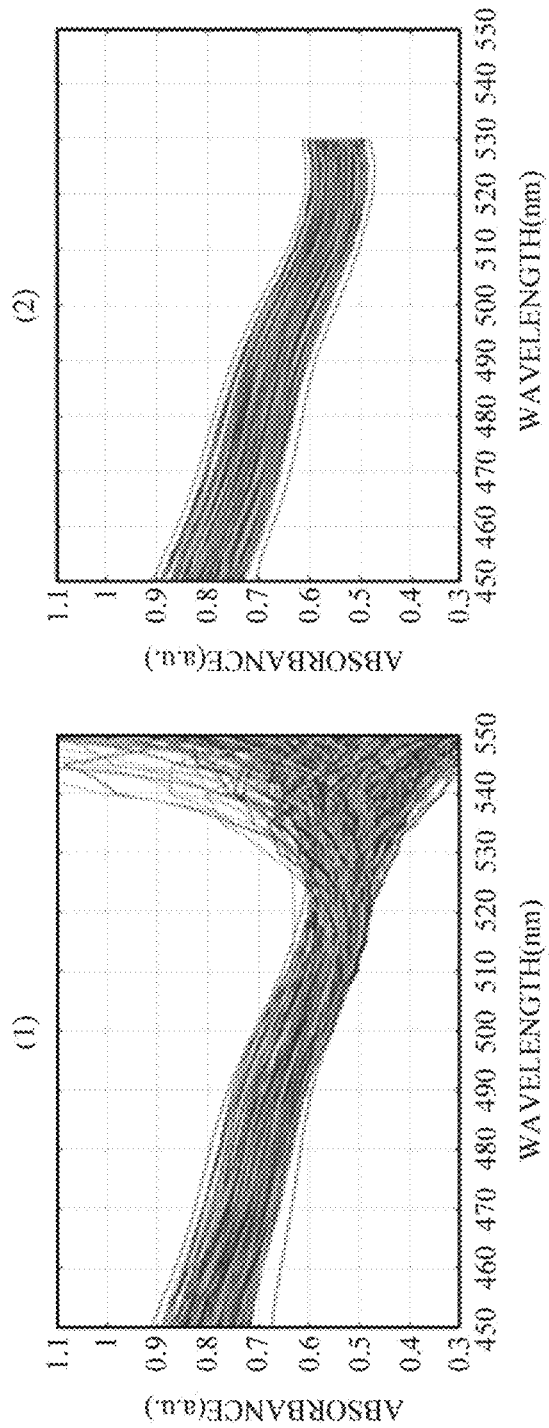

FIG. 4C is a diagram illustrating a correlation between the principal components PC2 and PC3, except for the pressure component PC1 among the principal components PC1, PC2, and PC3, and the estimated carotenoid values. Referring to FIG. 4C, it can be seen that the second principal component PC2 has a relatively low correlation with the estimated carotenoid values, and the third principal component PC3 has a relatively high correlation with the estimated carotenoid values. In this case, the processor 120 may determine the third principal component PC3, having a correlation greater than or equal to a predetermined threshold, to be a noise component. By removing the determined noise component PC3 from the entire first spectrum or from a spectrum after the initial pressure phase, the processor 120 may obtain a spectrum which less affected by the pressure change and the noise effect as illustrated in FIG. 4D.

Figure 5:
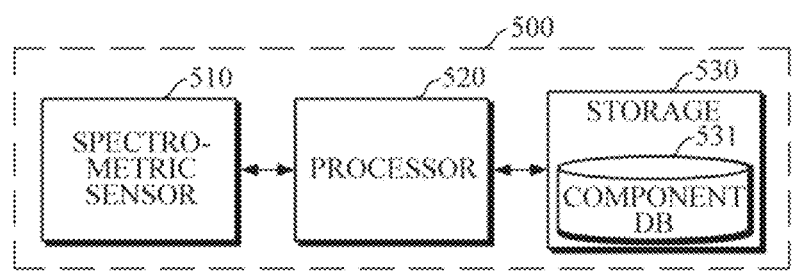
FIG. 5 is a block diagram illustrating an apparatus for estimating bio-information according to another embodiment.

FIG. 5 is a block diagram illustrating an apparatus for estimating bio-information according to another embodiment of the present disclosure.

Referring to FIG. 5, the apparatus 500 for estimating bio-information includes a spectrometric sensor 510, a processor 520, and a storage 530.

The spectrometric sensor 510 may include a light source and a detector as described above, and may continuously obtain light absorption spectra for a predetermined period of time.

The processor 520 may obtain first spectra based on the obtained spectrum data, and by referring to a component database (DB) 531 of the storage 530, the processor 520 may remove a component produced due to a pressure change of an object and/or a noise component from the first spectra.

For example, the processor 520 may perform principal component analysis by using second spectra obtained in an initial pressure phase. Further, the processor 520 may obtain a component, having a shape similar to a pressure component obtained from the component DB 531 among the principal components obtained by using principal component analysis, as the pressure component produced due to the pressure change of the object. By removing the pressure component from the entire first spectra or a spectrum after the initial pressure phase, the processor 520 may obtain a spectrum which is less affected by the pressure change of the object.

In another example, by referring to the storage 530, the processor 520 may obtain a pressure component, which represents a spectrum change caused by the pressure change of the object, from the component DB 531. The processor 520 may obtain a corrected spectrum by removing the pressure component, obtained from the component DB 531, from the first spectra.

In addition, the processor 520 may obtain a noise-related component from the component DB 531, and may remove the noise-related component from the first spectra or the spectrum after the initial pressure phase. Alternatively, the processor 520 may obtain a component, which is similar to the noise component stored in the component DB 531, from the result of principal component analysis of the second spectra, and may remove the obtained component from the first spectra or the spectrum after the initial pressure phase.

Further, the processor 520 may determine whether to use the component DB 531 based on a generation date and an update date of the component DB 531, a training data collection environment or a surrounding environment of a current user, and the like. In this case, the training data may refer to spectrum data obtained from a plurality of subjects. Further, the training data collection environment or the surrounding environment of the current user may include an age, sex, and a health condition of a subject, from which a spectrum is obtained, a surrounding environment (e.g., temperature, humidity, etc.) at a time when the spectrum is obtained, and the like.

For example, if an update date of the component DB 531 is within a predetermined period of time from a current time, the processor 520 may correct a spectrum by immediately using the pressure component obtained from the component DB 531. In another example, even when the update date is within the predetermined period of time, if the training data collection environment is substantially different from the surrounding environment of the current user, then the processor 520 may correct a spectrum by comparing the result of principal component analysis of the spectrum, obtained from the current user, with a spectrum shape of the pressure component obtained from the component DB 531. In yet another example, in the case where it is determined that data of the component DB 531 is unreliable, as in the case where the update date is within a predetermined period of time, the processor 520 may correct the spectrum by obtaining a pressure component based on the result of principal component analysis of the spectrum and a shape of the hemoglobin absorption peak as described above. These examples are intended to assist in understanding of the present disclosure and should not be interpreted as limiting the scope thereof.

The storage 530 may store the component DB 531, including a spectrum shape of the principal components which are analyzed by principal component analysis of a plurality of training data and/or principal component scores, and the like. In this case, the training data may be spectra obtained from a plurality of subjects; and the component DB 531 may manage the result of principal component analysis for a plurality of groups which are classified according to health condition, age, and/or sex of the plurality of subjects. By considering a user's age and sex, the processor 520 may obtain a pressure component and/or a noise component of a corresponding group when extracting a pressure component from the component DB 531.

In addition to the component DB 531, the storage 530 may store a variety of reference information related to spectrum processing. For example, the reference information may include criteria for determining whether to use the component DB 531, an initial pressure phase for principal component analysis, a bio-information estimation algorithm, and/or a user's health condition, age, and sex, and the like.

The storage 530 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

Further, as described above, the processor 520 may determine whether to update the component DB 531 based on a generation date and an update date of the component DB 531, a training data collection environment or a surrounding environment of a current user, and the like. For example, if a last update date of the component DB 531 is within a predetermined period of time, the processor 520 may determine to update the component DB 531.

For example, upon determining to update the component DB 531, the processor 520 may perform principal component analysis on spectra obtained from a user's object, and may update the component DB 531 based on the result of principal component analysis. The processor 520 may control the spectrometric sensor 510 a plurality of times at predetermined intervals, and may collect spectra, obtained from the user a plurality of number of times, as training data.

The processor 520 may replace existing data of the component DB 531 with data, including a pressure component obtained based on the principal component analysis result of the spectrum and a shape of the hemoglobin absorption peak, and/or a noise component determined based on a correlation between the principal component analysis result and an estimated bio-information value, and the like. Alternatively, the processor 520 may update the existing data of the component DB 531 by using data generated by combining data, obtained by principal component analysis, with the existing data of the component DB 531.

In another example, the processor 520 may obtain spectra, obtained from a plurality of subjects, as training data. Upon obtaining the spectra from the plurality of subjects, the processor 520 may analyze the principal component analysis result for each group by considering health condition, age, and/or sex of the plurality of subjects, and may update the component DB 531 by using the principal component analysis result of each group.

The processor 520 may provide a spectrum processing result for a user by using an output component. In this case, the output component may include a visual output component (e.g., a display, and the like), a audio output component (e.g., a speaker, and the like), a haptic component configured to provide vibrations, tactile sensation, and the like), and the like, but is not limited thereto. For example, the processor 520 may output a spectrum before correction, which is obtained from a user's object, the principal component analysis result, and/or a corrected spectrum to a display, and may divide the display into a plurality of areas to output the spectrum before correction and the spectrum after correction in various areas, so that the user may easily visually compare the spectra.

Further, based on receiving a request for the corrected spectrum from an external device, the processor 520 may transmit the corrected spectrum to the external device via a communication interface. Alternatively, if it is determined to update the component DB 531, the processor 520 may receive a principal component analysis result from an external device which is specialized for performing principal component analysis for a plurality of subjects. In this case, examples of the external device may include an information processing device such as a smartphone, a tablet personal computer (PC), a desktop computer, a laptop computer, and the like, and may be a device having a function of estimating bio-information by using a spectrum.

The communication interface may communicate with the external device by using communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G) communication, fourth generation (4G) communication, fifth generation (5G) communication, and the like. However, the foregoing examples are exemplary and non-limiting.

Figure 6:
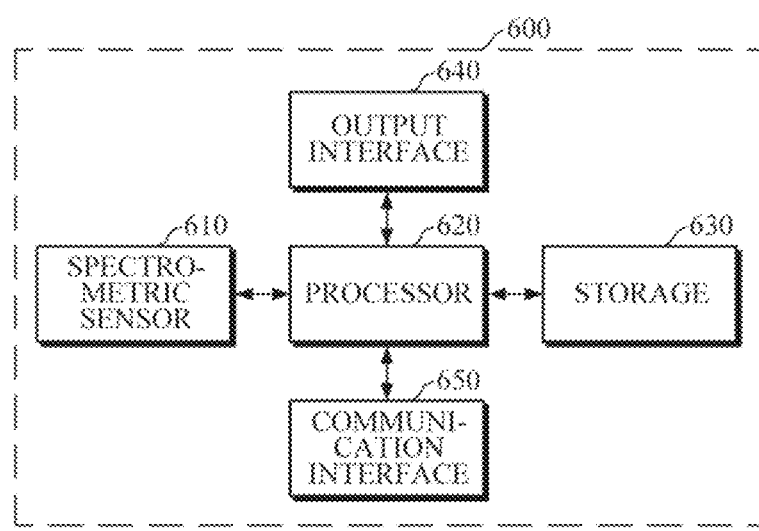
FIG. 6 is a block diagram illustrating an apparatus for estimating bio-information according to yet another embodiment.

FIG. 6 is a block diagram illustrating an apparatus 600 for estimating bio-information according to yet another embodiment of the present disclosure.

Referring to FIG. 6, the apparatus 600 for estimating bio-information includes a spectrometric sensor 610, a processor 620, a storage 630, an output interface 640, and a communication interface 650.

The spectrometric sensor 610 may obtain continuous spectra from a user's object. The spectrometric sensor 610 may include a light source and a detector. Under the control of the processor 620, the light source may emit light toward the object; and the detector may detect light reflected by the object after light is absorbed into, or scattered by, or reflected from, the object, may convert the detected light into an electric signal indicating light intensity, and may transmit the signal to the processor 620.

The processor 620 may be electrically connected to the spectrometric sensor 610 and various other components 630, 640, and 650, to control the operation thereof.

In response to a user's input or at predetermined bio-information estimation intervals, the processor 620 may control the spectrometric sensor 610, and may recover a spectrum by receiving spectrum data obtained by the spectrometric sensor 610.

For example, based on recovering the spectrum, the processor 620 may perform principal component analysis by using some group of spectra obtained in an initial pressure phase; and by using the principal component analysis result, the processor 620 may extract a pressure component of the object, i.e., a component produced due to a spectrum change caused by a pressure change of the object when the object comes into contact with the spectrometric sensor and applies pressure thereto.

In another example, when the component DB is included in the storage 630, the processor 620 may obtain a pressure component by referring to the component DB. In this case, the processor 620 may use the pressure component obtained from the component DB, and may obtain the pressure component of the object from the principal component analysis result based on comparing the principal component analysis result of the spectrum, obtained by the spectrometric sensor 610, with the pressure component obtained from the component DB. In this case, criteria for determining whether to use the component DB may be predetermined based on, for example, a generation date and an update date of the component DB, a training data collection environment or a surrounding environment of a user, and the like.

In addition, the processor 620 may determine whether to update the component DB based on a generation date and an update date of the component DB, a training data collection environment or a surrounding environment of a user, and the like. For example, based on determining to update the component DB, the processor 620 may update the component DB based on the principal component analysis result of the spectrum obtained from the user. In another example, the processor 620 may receive the component DB from an external device via the communication interface 650.

Further, by removing the obtained pressure component from the spectrum obtained by the spectrometric sensor 610, the processor 620 may correct a spectrum change caused by a pressure change of the object.

Moreover, the processor 620 may extract a noise-related component other than the pressure component of the object, and may obtain more accurate spectrum by further removing the extracted component. In this case, the noise-related component may be obtained by principal component analysis of the spectrum or based on the component DB, which is described above in detail.

By using the corrected spectrum, the processor 620 may estimate bio-information, such as blood glucose, triglyceride, cholesterol, calories, protein, carotenoid, lactate, uric acid, and the like. However, the estimation of bio-information is not limited thereto. For example, an estimation model may be pre-defined, which represents a correlation between the corrected spectrum and bio-information to be obtained. The processor 620 may estimate bio-information based on the corrected spectrum and the estimation model.

The storage 630 may store the component DB 631 and a variety of reference information related to estimating bio-information. For example, the reference information may include criteria for determining whether to use the component DB 631, an initial pressure phase for principal component analysis, a bio-information estimation algorithm and/or a user's health condition, age, and sex, and the like, but is not limited thereto.

The output interface 640 may provide a user with a processing result of the processor 620. In this case, the output interface 640 may include a visual output interface (e.g., a display, and the like), an audio output interface (e.g., a speaker, and the like), a haptic output interface configured to provide vibrations, tactile sensation, and the like), and the like, but is not limited thereto.

The communication interface 650 may communicate with an external device to transmit and receive data related to estimating bio-information. For example, the communication interface 650 may transmit spectra before and after correction, a principal component analysis result, a bio-information estimation result, and the like, to the external device, and may receive a component DB and the like from the external device. In this case, examples of the external device may include an information processing device such as a smartphone, a tablet PC, a desktop computer, a laptop computer, and the like, but is not limited thereto.

Figure 7:
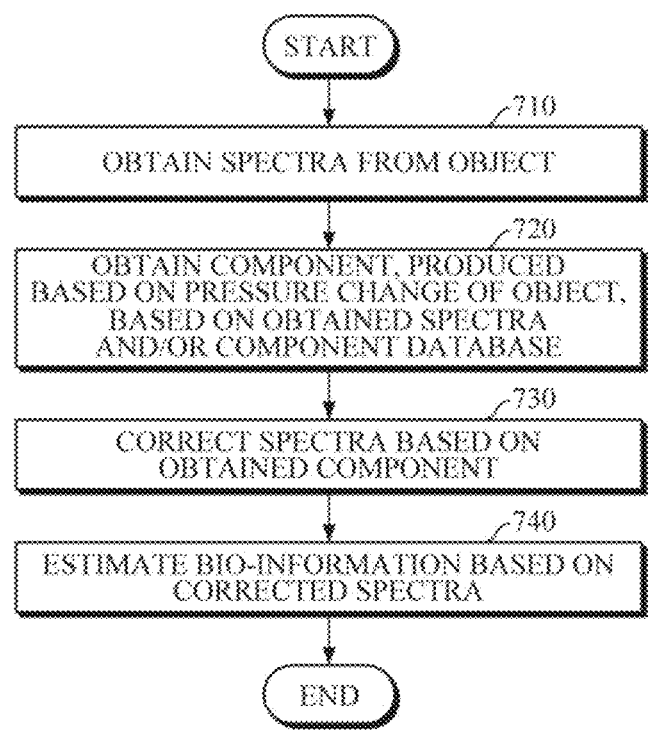
FIG. 7 is a flowchart illustrating a method of estimating bio-information according to an embodiment.

FIG. 7 is a flowchart illustrating a method of estimating bio-information according to an embodiment of the present disclosure.

FIG. 7 is an example of the method of estimating bio-information that is performed by the apparatus for estimating bio-information according to the embodiments described above, which is described in detail above, and thus will be briefly described below.

The apparatus for estimating bio-information may obtain spectra from an object in operation 710. The apparatus 100 for estimating bio-information may control a spectrometric sensor to continuously obtain spectrum data from the object for a predetermined period of time.

Then, the apparatus for estimating bio-information may obtain a component, produced based on a pressure change of the object, based on the obtained spectra and/or a component DB in operation 720.

For example, as described above with reference to FIG. 1, based on obtaining the spectra, the apparatus 100 for estimating bio-information may perform principal component analysis by using some group of spectra obtained in an initial pressure phase; and by using the principal component analysis result, the apparatus 100 for estimating bio-information may obtain a pressure component produced based on a pressure change of the object. For example, a shape of a hemoglobin absorption peak changes as the object applies pressure, such that the apparatus 100 for estimating bio-information may obtain a component, having a spectrum shape similar to an already known hemoglobin absorption peak among spectrum shapes of the principal components of the spectrum, as the pressure component.

In another example, as described above with reference to FIG. 5, based on obtaining the spectra, the apparatus 500 for estimating bio-information may obtain a pressure component from a pre-generated component DB. Alternatively, the apparatus 500 for estimating bio-information may perform principal component analysis on the spectra obtained in operation 710, and may obtain a component, having a spectrum shape similar to a shape of a pressure component stored in the component DB among spectrum shapes of the principal components, as a pressure component produced based on the pressure change of the object.

Then, the apparatus 500 for estimating bio-information may correct the spectra based on the obtained pressure component in operation 730. For example, by removing the pressure component obtained in operation 720 from the spectra obtained in operation 710 by using techniques such as a least square method, and the like, the apparatus 500 for estimating bio-information may correct a spectrum change caused by the pressure change of the object.

Subsequently, the apparatus 500 for estimating bio-information may estimate bio-information based on the corrected spectra in operation 740.

Figure 8:
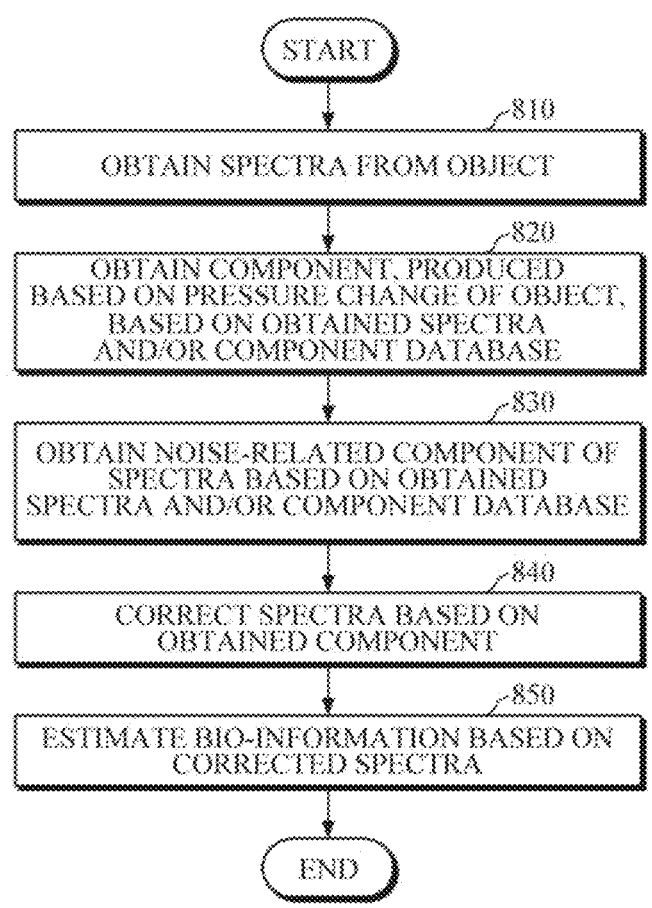
FIG. 8 is a flowchart illustrating a method of estimating bio-information according to another embodiment.

FIG. 8 is a flowchart illustrating a method of estimating bio-information according to another embodiment of the present disclosure.

FIG. 8 is an example of a method of estimating bio-information that is performed by the apparatus for estimating bio-information according to the embodiments described above, which is described in detail above, and thus will be briefly described below.

The apparatus for estimating bio-information may obtain spectra from an object in operation 810. The apparatus 100 for estimating bio-information may control a spectrometric sensor to continuously obtain spectrum data from the object for a predetermined period of time.

Then, the apparatus for estimating bio-information may obtain a component produced based on a pressure change of the object, based on the obtained spectra and/or a component DB in operation 820.

Subsequently, the apparatus for estimating bio-information may obtain a noise-related component, other than the component produced based on the pressure change of the object, based on the obtained spectra and/or the component DB in operation 830. For example, the apparatus for estimating bio-information may obtain a component, having a high correlation between the principal component scores of the principal components and an estimated bio-information value, as the noise-related component. In another example, the apparatus for estimating bio-information may obtain a noise-related component from the component DB. Alternatively, the apparatus for estimating bio-information may perform principal component analysis on the spectra obtained in operation 810, and may obtain a component, having a spectrum shape similar to a shape of a noise-related component stored in the component DB among spectrum shapes of the principal components, as the noise-related component.

Next, the apparatus for estimating bio-information may correct the spectra based on the obtained pressure component in operation 840. For example, the apparatus for estimating bio-information may correct a spectrum change by removing the pressure component obtained in operation 820 and the noise-related component obtained in operation 830 from the spectra obtained in operation 810 by using techniques such as a least square method, and the like.

Then, the apparatus for estimating bio-information may estimate bio-information based on the corrected spectra in operation 850.

Figure 9:
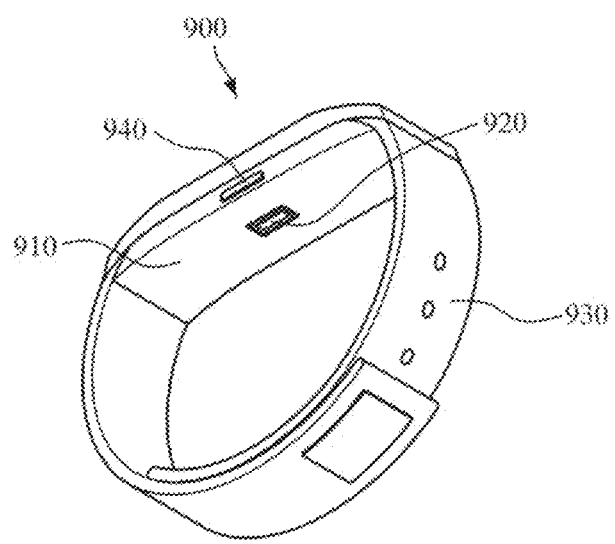
FIG. 9 is a diagram illustrating an example of a wearable device, to which embodiments of an apparatus for estimating bio-information may be applied.

FIG. 9 is a diagram illustrating an example of a wearable device, to which embodiments of an apparatus for estimating bio-information are applied.

The apparatuses 100, 500, and 600 for estimating bio-information according to the embodiments described above may be mounted in the wearable device 900. While FIG. 9 illustrates a smart watch-type wearable device 900, the wearable device is not limited thereto, and may be modified to various information processing devices such as a smartphone, a tablet PC, and the like.

Referring to FIG. 9, the wearable device 900 includes a main body 910 and a strap 930 and various modules of the aforementioned apparatuses 100, 500, and 600 for estimating bio-information may be mounted in the main body 910.

The strap 930 may be made of flexible material and may be connected to the main body 910.

The strap 930 may be bent to be wrapped around a user's wrist or may be bent in a manner which allows the strap 930 to be detached from the wrist. In this case, a battery may be embedded in the main body 910 or the strap 930 to supply power to the wearable device 900.

As illustrated in FIG. 9, a spectrometric sensor 920 may be mounted on a rear surface of the main body 910 at a position which contacts a user's wrist. For example, the spectrometric sensor 920 may include a Linear Variable Filter (LVF) having spectral properties which vary linearly over the entire length.

A processor, a storage, and a communication interface may be mounted in the main body 910 of the wearable device 900.

The processor may correct spectra, obtained by the spectrometric sensor 920, by principal component analysis, and may estimate bio-information based on the corrected spectra.

A display of an output interface may be mounted on a front surface of the main body 910, and may output a variety of information for a user. Further, the display may include a touch screen for receiving a user's touch input, and may receive the touch input and transmit the touch input to the processor.

In addition, the main body 910 of the wearable device 900 may include an input component 940 for operating a function of estimating bio-information and various other functions of the wearable device 900 (e.g., a clock application, a music application, data video application, a text messaging application, etc.). The input component 940 may receive a user's input and may transmit the input to the processor. Further, the input component 940 may include a power button to turn on/off the wearable device 900.

The present disclosure may be realized as computer-readable code stored on a non-transitory computer-readable medium. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium may be distributed over a plurality of computer systems connected to a network so that computer-readable code is written thereto and executed therefrom in a decentralized manner. Functional programs, code, and code segments for realizing the present disclosure can be deduced by one of ordinary skill in the art.

The present disclosure has been described herein with regard to various embodiments. However, it will be obvious to those skilled in the art that various changes and modifications can be made without departing from the technical concepts of the present disclosure. Thus, it is clear that the above-described embodiments are illustrative in all aspects and are not intended to limit the present disclosure.

What is claimed is:

1. An apparatus for estimating bio-information, the apparatus comprising:
    a processor configured to:
        obtain spectra from an object;
        perform principal component analysis (PCA) on the obtained spectra;
        obtain a component, which is produced based on a change in pressure applied to the object, based on a result of performing the PCA;
        correct the spectra based on the obtained component produced based on the change in pressure; and
        estimate the bio-information of the object based on the corrected spectra.

2. The apparatus of claim 1, wherein the processor is configured to:
obtain the component, produced based on the change in pressure, based on a shape of components which are analyzed by using the PCA.

3. The apparatus of claim 2, wherein the processor is further configured to:
obtain the component, having a shape similar to a hemoglobin absorption peak among the components analyzed by using the PCA, as the component produced based on the change in pressure.

4. The apparatus of claim 2, wherein the processor is further configured to:
obtain the component, having a spectrum shape similar to that of a component defined in a component database among the components analyzed by the PCA, as the component produced based on the change in pressure.

5. The apparatus of claim 1, wherein the processor is further configured to:
obtain the component from a component database, based on the result of performing the PCA.

6. The apparatus of claim 5, wherein the processor is further configured to:
collect spectra, obtained from a plurality of subjects, as training data;
perform the PCA on the collected training data; and
store a spectrum shape of principal components and principal component scores in the component database based on performing the PCA.

7. The apparatus of claim 6, wherein the processor is further configured to:
perform the PCA on the obtained spectra from the object; and
update the component database by using the components analyzed by using the PCA.

8. The apparatus of claim 7, wherein the processor is further configured to:
determine whether to update the component database based on at least one of the result of performing the PCA on the spectra obtained from the object, a generation date and an update date of the component database, and a collection environment of the training data.

9. The apparatus of claim 8, further comprising a communication interface which, in response to determining to update the component database, receives data from an external device.

10. The apparatus of claim 1, wherein the component corresponds to a first component, and the obtained spectra comprises the first component and a second component, and wherein the processor is further configured to:
correct a spectrum change caused by the change in pressure by removing the second component, produced based on the change in pressure, from the obtained spectra; and
obtain the first component based on the corrected spectrum change.

11. The apparatus of claim 10, wherein the processor is further configured to:
remove the second component from the obtained spectra by using a least square method.

12. The apparatus of claim 1, wherein the processor is further configured to:
obtain the component, produced based on the change in pressure, based on spectra obtained during an initial pressure phase of an entire time period in which the spectra are obtained.

13. The apparatus of claim 1, wherein the processor is further configured to:
obtain a noise-related component of the obtained spectra; and
correct the obtained spectra based on the component produced based on the change in pressure and the noise-related component.

14. The apparatus of claim 13, wherein based on a correlation between principal component scores of principal components, which are analyzed by performing principal component analysis on at least one spectrum of the obtained spectra, and an estimated bio-information value which is estimated based on the at least one spectrum of the spectra, the processor is further configured to:
obtain at least one of the component produced based on the change in pressure and the noise-related component.

15. The apparatus of claim 1, wherein the bio-information of the object includes at least one of blood glucose, triglyceride, cholesterol, calories, protein, carotenoid, lactate, and uric acid.

16. A method of estimating bio-information of an object, the method comprising:
obtaining spectra from the object;
performing principal component analysis (PCA) on the obtained spectra;
obtaining a component, which is produced based on a change in pressure applied to the object, based on a result of the PCA;
correcting the spectra based on the obtained component produced based on the change in pressure; and
estimating the bio-information of the object based on the corrected spectra.

17. The method of claim 16, wherein the obtaining of the component produced based on the change in pressure comprises obtaining the component, produced based on the change in pressure, based on a shape of components which are analyzed by using the PCA.

18. The method of claim 17, wherein the obtaining of the component produced due to the change in pressure comprises obtaining the component, having a shape similar to a hemoglobin absorption peak among the components analyzed by using the PCA, as the component produced based on the change in pressure.

19. The method of claim 17, wherein the obtaining of the component produced based on the change in pressure comprises obtaining a component, having a spectrum shape similar to that of a component defined in a component database among the components analyzed by the PCA, as the component produced based on the change in pressure.

20. The method of claim 16, wherein the obtaining of the component produced based on the change in pressure comprises obtaining the component from a component database, based on the result of performing the PCA.

21. The method of claim 16, wherein the correcting of the spectra comprises correcting a spectrum change caused by the change in pressure by removing the component, produced based on the change in pressure, from the obtained spectra.

22. The method of claim 16, wherein the obtaining of the component produced based on the change in pressure comprises obtaining the component, produced based on the change in pressure, based on spectra obtained during an initial pressure phase of an entire time period in which the spectra are obtained.

23. The method of claim 16, further comprising:
obtaining a noise-related component of the obtained spectra,
wherein the correcting of the spectra comprises correcting the obtained spectra based on the component produced based on the change in pressure and the noise-related component.

24. The method of claim 23, wherein the obtaining of the noise-related component comprises obtaining the noise-related component based on a correlation between principal component scores of principal components, which are analyzed by performing principal component analysis on at least one spectrum of the obtained spectra, and an estimated bio-information value which is estimated based on the at least one spectrum of the spectra.

25. A non-transitory computer-readable medium storing instructions, the instructions comprising:
one or more instructions that, when executed by one or more processors of a device, cause the one or more processors to:
obtain spectra from an object via a spectrometric sensor;
perform principal component analysis (PCA) on the obtained spectra;
obtain a component, which is produced based on a change in pressure applied to the object, based on a result of performing the PCA;
correct the spectra based on the obtained component produced based on the change in pressure; and
estimate bio-information of the object based on the corrected spectra.

* * * * *